United States Patent [19]

Rockwell

[11] Patent Number: 4,610,825

[45] Date of Patent: Sep. 9, 1986

[54] PHOSPHOROUS ACID CATALYZED PHENOL ESTERIFICATION

[75] Inventor: Ned M. Rockwell, Gurnee, Ill.

[73] Assignee: Stepan Company, Northfield, Ill.

[21] Appl. No.: 724,172

[22] Filed: Apr. 17, 1985

[51] Int. Cl.$^4$ ............... C09F 5/08; C09F 7/10; C11C 3/00; C07C 67/08
[52] U.S. Cl. ................... 260/410.5; 560/130
[58] Field of Search ............ 260/410.5; 502/155, 502/208; 560/130

[56] References Cited

U.S. PATENT DOCUMENTS

| | | | |
|---|---|---|---|
| 2,622,071 | 12/1952 | Harrison | 525/451 |
| 2,822,378 | 2/1958 | Bader | 260/410.5 |
| 3,106,570 | 10/1963 | Jaruzelski et al. | 260/410.5 |
| 3,772,389 | 11/1973 | Lowrance | 260/465 D |
| 4,271,311 | 6/1981 | Knickmeyer et al. | 560/86 |
| 4,289,896 | 9/1981 | Buxbaum | 260/410.5 |
| 4,465,633 | 8/1984 | Goel et al. | 260/410.5 |
| 4,478,754 | 10/1984 | Kong-Chan | 260/410.5 |

OTHER PUBLICATIONS

Van Wazer article "Phosphorus and Its Compounds" from Interscience Publishers, Inc., New York, 1958, vol. 1, p. 371.
Kirk-Othmer Encyclopedia of Chemical Technology, third edition, vol. 17, "Peroxides and Peroxy Compounds, Inorganic to Piping Systems" a Wiley-Interscience Publication, John Wiley & Sons, pp. 490-491, 539.
Chemical Technicians' Ready Reference Handbook from the McGraw-Hill Book Company, pp. 122-123.
The Merck Index, An Encyclopedia of Chemicals, Drugs, and Biologicals, tenth edition, published by Merck & Co., Inc. New Jersey, 1983, pp. 7231.
Stauffer Chemical Company data sheet for $H_3PO_3$.
*Chem. Abstracts* 92:23463s.
*Chem. Abstracts* 94:121112n.
*Chem. Abstracts* 98:145463m.
David Aelony article, "Direct Esterification of Phenols with Higher Fatty Acids" from *The Journal of the American Oil Chemists' Society*; vol. 32, pp. 170-172.
Conant and Blatt article, "The Chemistry of Organic Compounds" from the MacMillan Company, New York, 1947, third edition, pp. 430-431.
Chamberlain, Ph.D. article, "A Textbook of Organic Chemistry" from the Philadelphia P. Blakiston & Co., Inc. third edition, pp. 480-481.

*Primary Examiner*—Natalie Trousof
*Assistant Examiner*—Patricia M. Scott
*Attorney, Agent, or Firm*—Hill, Van Santen, Steadman & Simpson

[57] ABSTRACT

A phosphorous acid or mixture of phosphorous acids is used as catalyst in the esterification reaction of phenol and carboxylic acids. Water is removed from the reaction zone in an efficient manner. An ester product of high purity and excellent color with minimal by-products is characteristically produced.

12 Claims, No Drawings

PHOSPHOROUS ACID CATALYZED PHENOL ESTERIFICATION

BACKGROUND OF THE INVENTION

1. Field of the Invention

This invention lies in the field of methods for the production of esters from phenolic compounds and carboxylic acids.

2. Description of the Prior Art

Various catalysts and catalyst systems have heretofore been taught for the esterification of compounds having phenolic hydroxyl groups with organic carboxylic acids.

For examples, Kong-Chan U.S. Pat. No. 4,478,754 teaches the uses of boric anhydride as the catalyst to make sulfonated carboxylic acid esters of phenol; Lowrence U.S. Pat. No. 3,772,389 uses a catalyst system of boron compound and sulfonic acid; and Knickmeyer et al U.S. Pat. No. 4,271,311 discloses a catalyst system of boron compound and certain alkali metal salts.

The use of aliphatic and aromatic esters of phosphorous acid as catalysts is taught in Harrison U.S. Pat. No. 2,622,071. No mention or suggestion of using inorganic phosphorous acids as catalysts is made.

All of such prior art catalysts and catalyst systems, and the phenolic esterification processes employing such, result so far as now known in the production of ester products which are in an impure state with such product being characteristically significantly colored and being in admixture with undesired by-products, the latter being produced, it appears, mainly by Fries rearrangement. Before these prior art ester products can be used, for example, as starting materials for sulfonation to produce sulfonated carboxylic acid esters of phenol, they must be purified and decolored in order to result in a final product of commercially acceptable quality.

There is a need in the art for a new and improved catalyst which permits production of high purity, low color ester from starting materials comprising phenolic compounds and carboxylic acids.

BRIEF SUMMARY OF THE INVENTION

More particularly, my present invention relates to a process for directly esterifying a compound having a phenolic hydroxyl group with an organic carboxylic acid in the presence of a catalytically effective amount of an inorganic phosphorous acid, or mixture of inorganic phosphorous acids.

Briefly, a mixture of such reactants is heated in such presence at an elevated temperature which is below the decomposition temperature of such reactants and reaction products, and water is concurrently removed from the reaction mass.

An object of this invention is to provide a new and improved process for catalytically directly esterifying phenolic compounds with carboxylic acids in a highly efficient manner so that high rates of conversion are obtainable in relatively short reaction times.

Another effect is to provide, in a process of the class indicated, a new catalyst which permits production of product phenyl ester of sufficient quality and purity to be further processed into a desired end-product without the need for an intervening purification, or like, step.

Another object is to provide such a process as indicated above which is simple to practice, extremely reliable, and adaptable for practice in conventional processing equipment.

Another object is to provide such a process as indicated above which can be practiced to produce an ester product which is either substantially uncolored (or colorless) or is only slightly colored (yellow in hue).

Another object is to provide such a process as indicated above which can be practiced to produce an ester product which contains only minimal amounts of undesirable by-products, such as by-products produced by so-called Fries rearrangement.

Another object is to provide such a process as indicated above which when practiced in conventional reactor equipment, is less corrosive to standard materials of construction than, for example, prior art sulfuric-boric acid catalyst systems.

Another object is to provide, for a process of the type above indicated, a catalyst system which is low cost, simple to prepare and use and adapted for use in commercial scale esterification of phenol.

Other and further aims, objects, purposes, advantages, uses, and the like for the present invention will be apparent to those skilled in the art from the present invention.

DETAILED DESCRIPTION

Catalysts

The catalyst employed in the practice of this invention comprises a phosphorous acid compound or mixture of phosphorous acid compounds, such as a material selected from the group consisting of:

(a) phosphorous acid,
(b) phosphite salts which display an acidic pH in aqueous solution, and
(c) mixtures thereof.

A present preference when a phosphite salt is employed is to use one wherein the cation is selected from the group consisting of alkali metals, alkaline earth metals, and ammonium. Sodium and/or potassium cations are particularly preferred. A presently most preferred catalyst comprises ortho phosphorous acid.

The catalyst can be in aqueous solutions or slurry if desired initially.

A phosphorous acid compound (that is, and/or phosphite salt and/or mixture of such) is considered to be any phosphorous compound containing the combination of P—H bond(s), P=O bond(s) and P—O—H bond(s). Examples of such phosphorous and phosphite salt compounds are depicted as follows:

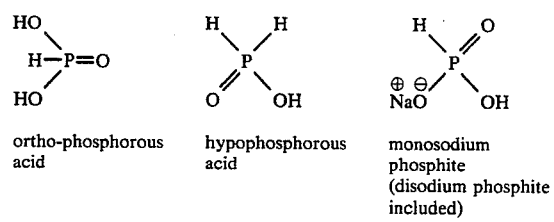

ortho-phosphorous acid hypophosphorous acid monosodium phosphite (disodium phosphite included)

Starting Materials

Organic carboxylic acids employed as starting materials in the practice of this invention are typically characterized by the generic formula:

RCOOH  (1)

where R is a hydrocarbyl radical containing from 1 to 19 carbon atoms.

The hydrocarbyl group need have no special or particular characteristics. It can be saturated or unsaturated, a straight or branched chain, aliphatic or aromatic or mixture thereof, and substituted or unsubstituted. When substituted, the substituent can be at least one radical selected from the group consisting of halogen (chloride being one example), nitro, and alkoxy. Alkoxy radicals preferably contain less than seven carbon atoms each and less than three oxygen atoms each. Preferably R is an alkyl radical containing from 1 to 19 carbon atoms.

The hydrocarbyl group can also be substituted with a carboxyl group, so that the organic carboxylic acid can be, for example, hexanedioic acid or the like. However, the rate and conversion obtained by using dibasic carboxylic acids is not as appreciable as those obtained by using monobasic carboxylic acids.

Examples of carboxylic acids include octanoic, nonanonic, isononanoic, decanoic, dodecanoic, fatty acids, and the like. Other carboxylic acids include resin acids, polycarboxylic acids, acetic acid, oxalic acid, benzoic acid, stearic acid, palmitic acid, mixtures thereof, and the like.

A present preference is to employ carboxylic acids which contain at least about 4 carbon atoms per molecule.

More preferably, in formula (1) above, R is an alkyl radical containing from 8 through 12 carbon atoms.

A phenol compound employed as a starting material in the practice of the present invention is characterized by being an aromatic compound which has at least one ring substituted reactive hydroxyl group and which has at least one unsubstituted carbon atom adjacent the carbon atom bearing such hydroxyl group(s). Such a compound does not contain additional substituents bonded to the ring which hinder (prevent) the reacting of such hydroxyl group with the acid.

Preferably, a phenol compound contains less than 5 reactive hydroxyl groups. A presently most preferred phenolic compound comprises phenol. Examples of other suitable monomeric phenol compounds include naphthol, cresol, para-tert-butyl phenol, p-phenyl phenol, and the like. Examples of polymeric phenol compounds include phenol-formaldehyde resins, and the like.

In general, a phenol compound is in a liquid state under the conditions of contacting (reacting) with the organic carboxylic acid in the practice of the process of the present invention.

Process Conditions

Esterification in accord with this invention is effected by introducing at least one phenol compound, at least one organic carboxylic acid, and phosphorous acid compound (as catalyst) into a reaction zone (e.g., a vessel). Mixing of such reactants can be accomplished by any conventional procedure.

Although very small amounts of the herein employed catalyst appear to be effective, it is presently preferred to employ at least about 0.1% by weight of the catalyst based on the weight of phenol compound employed in order to obtain appreciable reaction rates. In general, catalyst concentrations above about 5% are not efficient for industrial production and begin to have detrimental effects on the desired reaction.

In the reaction zone, the mole ratio of phenol compound to organic carboxylic acid can range widely, but preferably either the phenol compound or the organic carboxylic acid is always present in an excess amount over stoichiometry to favor ester formation. A presently preferred such mole ratio of phenol compound to organic carboxylic acid compound ranges from about 0.8 to 1.2.

As the esterification reaction proceeds, water is produced. The water from reaction is removed from the reaction zone, preferably in the most efficient manner. If desired, an azeotropic material can be present to aid in water removal such as toluene, xylene, benzene or other hydrocarbons which boil in about the same temperature range/pressure. Preferably the process is conducted under any combination of temperature and pressure conditions such that vapor containing water is constantly liberated during the reaction and removed.

A present preference is to employ a temperature in the range from about 100° to 250° C., and preferably from about 180° C. to 240° C., but higher and even lower temperatures can be used within the degradation limits of the materials, if desired. Pressure is preferably and conveniently atmospheric or lower, although pressures greater than atmospheric are feasible if properly contained. Thus, suitable subatmospheric pressures range from about 760 to 10.0 mmHg while optional superatmospheric pressures range from about 0.1 to 15 psig.

The extent of conversion can be determined by any convenient procedure, such as, for example, measuring to determine the concentration of the limiting reagent.

Reactants can be maintained in a reaction zone under the elevated temperature conditions (and pressure, if used) indicated above either until a desired or substantially complete conversion of reactants to ester product is obtained, or until by-product formation reaches a level considered (in any given case) to be significant.

Characteristically, the process of this invention results in a higher conversion of a given set of reactants to desired ester product before Fries rearrangements to produce undesired by-products occur to an undesired level. It is presently preferred to continue the heating and the water removal by the practice of the present invention until the total content of Fries rearrangement by-products is not more than about 5%.

At the end of the contacting period in the reaction zone, one can, if desired, strip off residual unreacted starting materials by conventional distillation procedures. The conditions used are dependent upon the compounds involved, as those skilled in the art will appreciate. For example, when phenol is reacted as taught herein with a carboxylic acid of formula (1), the product can be distilled; convenient conditions comprise use of temperatures in the range from about 100° to 250° C. using pressures in the range from about 760 to 0.1 mm Hg, although an optimized temperature and pressure for a particular phenol carboxylate ester would vary, being dependent upon the particular structure of a given such product.

The catalyst appears to be readily soluble in a reaction product. However, if a catalyst-free product is desired, the product itself (preferably after stripping to remove unreacted starting materials) can be distilled, condensed and collected. The strong reducing activity characteristic of the phosphorous catalyst compounds is also beneficial with regard to the color of the phenyl ester products. Indeed, relatively dark color phenols and carboxylic acids may be used to produce a very light colored undistilled phenyl ester. Distillation of such crudes yields phenyl esters on the order of 5–20 APHA color.

Although water can be initially present in a reasonable amount (e.g. not more than about 10 wt. % based upon total weight of a starting reactant mixture), those skilled in the art will appreciate that during the esterification procedure of this invention, the water initially present will be removed, preferably continuously as hereinabove described.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

Unless otherwise noted, only substantially anhydrous starting materials and catalysts are employed in the following Examples.

EXAMPLE 1

1082 grams (7.5 moles) of approximately 95% octanoic acid (the balance being hexanoic acid and decanoic acid), 1410 grams (15.0 moles) phenol, and 24.6 grams ortho-phosphorous acid (anhydrous crystals) are charged to a four-necked, five liter round-bottom flask fitted with a nitrogen sparge leg, thermometer, mechanical stirrer, and a rectifying column. The flask is heated at about 40° to 245° C. using a heating mantle under a subtle nitrogen sparge with constant agitation. Water from reaction is liberated throughout the reaction and is removed via the rectifying column continuously. The reaction is terminated after 10.5 hours by stopping the heat input and cooling. Thereafter stripping is carried out to remove excess reagents by vacuum distillation using temperatures ranging from about 50° to 200° C. and pressures ranging from about 760 to 0.1 mm Hg. The stripped mixture is then vacuum distilled. From acid value analysis of the distillate, it is determined that conversion of the carboxylic acid is approximately 97%, and production of the desired phenyl esters is approximately 95% of the potential amount available from the initial charge of carboxylic acids as determined from gas chromatographic analysis.

EXAMPLE 2

The same charge, procedure and conditions as used in Example 1 are followed with the exception that the reaction is run for fifteen hours. Analyses showed that conversion of the carboxylic acids is approximately 98%, and production of the desired phenyl esters is approximately 95% of the potential amount available from the initial charge of carboxylic acids.

EXAMPLE 3

1136 grams (7.5 moles) of a mixture of approximately 55% octanoic acid, 39% decanoic acid, 5% hexanoic acid, and 1% dodecanoic acid is charged along with 869 grams (9.25 moles) phenol and 24.6 grams ortho-phosphorous acid (anhydrous). The same setup and conditions as in the previous examples are used. The reaction is run for thirteen hours and followed immediately by vacuum distillation. Analyses show that conversion of the carboxylic acids is approximately 92%, and production of the desired phenyl esters is approximately 89% of the potential amount available from the initial charge of the carboxylic acids.

EXAMPLE 4

1207 grams (7.5 moles) of nonanoic acid, 869 grams (9.25 moles) phenol, and 24.6 grams of ortho-phosphorous acid is charged to the same setup and conditions as in the previous examples. The reaction is run for thirteen hours and followed immediately by distillation. Analyses showed that conversion of the carboxylic acid is approximately 92%, and the production of the desired phenyl ester is approximately 88% of the potential amount available from the initial charge of carboxylic acid.

EXAMPLE 5

(Prior Art)

1081 grams (7.5 moles) of approximately 95% octanoic acid (the balance being hexanoic acid and decanoic acid), 869 grams (9.25 moles) phenol, 12.3 grams sulfuric acid, and 12.3 grams boric acid are charged to the same setup and conditions as in the previous examples. The reaction is run for 11.5 hours and followed immediately by distillation. Analyses showed that conversion of the carboxylic acids is approximately 95%, and production of the desired phenyl esters is approximately 72%. This is an example of the non-selectivity of the sulfuric acid/boric acid catalyst system toward the desired phenyl ester product.

EXAMPLE 6

1081 grams (7.5 moles) of approximately 95% octanoic acid (the balance being hexanoic acid and decanoic acid), 869 grams (9.25 moles) phenol, and 24.6 grams of a 50 weight percent solution of hypophosphorous acid in water (i.e., 12.3 grams ($H_3PO_2$) are charged to the same setup and conditions as in the previous examples. The reaction was run for twelve hours and followed immediately by distillation. Analyses showed that conversion of the carboxylic acids is approximately 91%, and production of the desired phenyl esters is approximately 89% of the potential amount available from the initial charge of carboxylic acids.

EXAMPLE 7

1082 grams (7.5 moles) of approximately 95% octanoic acid (the balance being hexanoic acid and decanoic acid) 869 grams (9.25 moles) phenol, and 55 grams of a 55 weight percent aqueous solution of monosodium phosphite (i.e., 30 grams $NaH_2PO_3$) are charged to the same setup and conditions as in the previous examples. The reaction is run for twelve hours. Conversion and product yield were very similar to that of "Example 6".

EXAMPLE 8

1082 grams (7.5 moles) of approximately 95% octanoic acid (the balance being hexanoic acid and decanoic acid), 869 grams (9.25 moles) phenol, and 24.6 grams of an 85 weight percent aqueous solution of phosphoric acid are charged to the same setup and conditions as in the previous examples. The reaction is run for 10.3 hours. Conversion and product yield were only 75% of that obtained in "Example 1". This is an example of the relative catalytic inactivity of an acidic phosphorous compound which does not contain both P—H and P—O—H bonds.

EXAMPLE 9

1082 grams (7.5 moles) of approximately 95% octanoic acid (the balance being hexanoic acid and decanoic acid), 869 grams (9.25 moles) phenol, and 24.6 grams of a mixture of approximately 35 weight percent metaphosphoric acid and 65% NaPO$_3$ are charged to the same setup and conditions as in the previous examples. The reaction is terminated after three hours with relatively no conversion of carboxylic acid. This is another example of the inactive catalytic activity of an acidic phosphorous compound which does not contain both P—H and P—O—H bonds.

EXAMPLE 10

200 grams (1.4 moles) of approximately 95% octanoic acid (the balance being hexanoic acid and decanoic acid), 235.5 grams p-tert-butylphenol (1.6 moles), and 4.3 grams of orthophosphorous acid are charged to a flask fitted with a mechanical stirrer, thermometer, Dean-Stark trap, reflux condenser, and a nitrogen sparge leg. Toluene is used as an azeotrope to remove water from the reaction zone. The reaction is run for fourteen hours and followed by distillation. Gas chromatographic analysis indicated that the production of the desired phenyl esters is approximately 72% of the potential amount available from the initial charge of carboxylic acid.

EXAMPLE 11

200 (1.4 moles) grams of approximately 95% octanoic acid (the balance being hexanoic acid and decanoic acid), 344 grams of nonylphenol (1.6 moles), and 4.3 grams of ortho-phosphorous acid are charged to the same setup as mentioned in Example 6. Toluene is used as an azeotrope to remove water from the reaction zone. The reaction is run for ten hours and followed by distillation. Gas chromatographic analysis indicated that the production of the desired product phenyl esters is approximately 74% of the potential amount available from the initial charge of carboxylic acids.

EXAMPLE 12

200 grams (1.4 moles) of approximately 95% octanoic acid (the balance being hexahoic acid and decanoic acid), 169.6 grams p-oresol (1.6 moles), and 4.3 grams of ortho-phosphorous acid are charged to the same setup as mentioned in Example 6. Toluene is used as an azeotrope. The reaction is run for 9.5 hours and followed by distillation. Gas chromatographic analysis indicated that the production of the desired product phenyl esters is approximately 79% of the potential amount available from the initial charge of carboxylic acids.

As is apparent from the foregoing specification, the invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

I claim:

1. In a process for making a phenyl ester of a carboxylic acid, by heating a mixture of an organic carboxylic acid with a phenol compound in the presence of a catalyst while removing water from the so heated mixture, the improvement which comprises employing as said catalyst a catalytically effective amount of a material selected from the group consisting of (a) a phosphorous acid compound containing the combination of P—H, P=O and P—O—H bonds, (b) phosphite salts which display an acidic pH in aqueous solution, and (c) mixtures thereof.

2. The process of claim 1 wherein said organic carboxylic acid is characterized by the generic formula

RCOOH where R is a hydrocarbyl radical containing from 1 to 19 carbon atoms.

3. The process of claim 2 wherein R is an alkyl radical containing from 8 through 12 carbon atoms.

4. The process of claim 1 wherein said phenol compound contains from 1 through 4 aromatic ring substituted reactive hydroxyl groups and at least one unsubstituted carbon atom exists adjacent the carbon atoms bearing one such hydroxyl group.

5. The process of claim 4 wherein said phenol compound comprises phenol.

6. The process of claim 1 wherein the mole ratio of said phenol compound to said organic carboxylic acid ranges from about 0.8 to 1.2.

7. The process of claim 1 wherein the quantity of catalyst ranges from about 0.1 to 5% by weight based on the weight of said phenol compound.

8. The process of claim 1 wherein said heating is conducted at a temperature ranging from about 100° to 250° C.

9. The process of claim 8 wherein said heating is conducted while maintaining a subatmospheric pressure ranging from about 760 to 10 mmHg.

10. The process of claim 8 wherein said heating is conducted while maintaining a superatmospheric pressure ranging from about 0.1 to 15 psig.

11. The process of claim 1 wherein said heating and said removing are carried out until the total content of Fries rearrangement by-products is not more than about 5% of the total ester containing product mixture.

12. The process of claim 5 wherein after said contacting, the product of said heating and said removing is subjected to distillation at temperatures in the range from about 100° to 250° C. using pressures in the range from about 760 to 0.1 mm Hg.

* * * * *